US011478533B2

(12) United States Patent
Hansen et al.

(10) Patent No.: US 11,478,533 B2
(45) Date of Patent: Oct. 25, 2022

(54) SEMAGLUTIDE FOR USE IN MEDICINE

(71) Applicant: Novo Nordisk A/S, Bagsvaerd (DK)

(72) Inventors: Morten Hansen, Princeton, NJ (US); Martin Linder, Copenhagen (DK); Carl Richard Torstenson, Limhamm (DK); Mads Sundby Palle, Frederiksberg (DK); Lars Holm Damgaard, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/931,093

(22) Filed: May 13, 2020

(65) Prior Publication Data

US 2021/0330748 A1    Oct. 28, 2021

(30) Foreign Application Priority Data

Apr. 27, 2020  (EP) .................................... 20171536
May 6, 2020   (EP) .................................... 20173341

(51) Int. Cl.
  *A61K 38/26*   (2006.01)
  *A61P 1/16*    (2006.01)
  *A61K 9/00*    (2006.01)
  *A61K 47/10*   (2017.01)

(52) U.S. Cl.
  CPC ................ *A61K 38/26* (2013.01); *A61P 1/16* (2018.01); *A61K 9/0019* (2013.01); *A61K 47/10* (2013.01)

(58) Field of Classification Search
  CPC ...... A61K 38/26; A61K 47/10; A61K 9/0019; A61P 1/16
  See application file for complete search history.

(56) References Cited

U.S. PATENT DOCUMENTS

| 8,114,833 | B2 | 2/2012 | Pedersen et al. |
| 8,129,343 | B2 | 3/2012 | Lau et al. |
| 8,536,122 | B2 | 9/2013 | Lau et al. |
| 8,969,557 | B2 | 3/2015 | Harriman et al. |
| 10,888,605 | B2 | 1/2021 | Moeller et al. |
| 2012/0094894 | A1 | 4/2012 | Graefe-Mody et al. |
| 2013/0123230 | A1 | 5/2013 | Carpino et al. |
| 2013/0123231 | A1 | 5/2013 | Harriman et al. |
| 2013/0281373 | A1 | 10/2013 | Klein et al. |
| 2014/0221659 | A1 | 8/2014 | Kinzel et al. |
| 2015/0087585 | A1 | 3/2015 | Ahn et al. |
| 2015/0259323 | A1 | 9/2015 | Cabral et al. |
| 2016/0108060 | A1 | 4/2016 | Greenwood et al. |
| 2016/0108061 | A1 | 4/2016 | Greenwood et al. |
| 2016/0185783 | A1 | 6/2016 | Greenwood et al. |
| 2016/0185799 | A1 | 6/2016 | Greenwood et al. |
| 2017/0298112 | A1 | 10/2017 | Zimmer et al. |
| 2017/0348293 | A1 | 12/2017 | Miao et al. |
| 2018/0051012 | A1 | 2/2018 | Boehm et al. |
| 2018/0105498 | A1 | 4/2018 | Zemel et al. |

| 2019/0004066 | A1 | 1/2019 | Sarkar et al. |
| 2019/0055279 | A1 | 2/2019 | Kumar et al. |
| 2019/0321364 | A1 | 10/2019 | Satyal et al. |
| 2019/0367578 | A1 | 12/2019 | Hogendorf et al. |
| 2019/0388398 | A1 | 12/2019 | Foucart et al. |
| 2020/0071306 | A1 | 3/2020 | Esler et al. |
| 2020/0121625 | A1 | 4/2020 | Walczak et al. |
| 2021/0252111 | A1 | 8/2021 | Engelund et al. |

FOREIGN PATENT DOCUMENTS

| WO | 2003015//1 | A1 | 2/2003 |
| WO | 2003015777 | A1 | 2/2003 |
| WO | 2003016280 | A1 | 2/2003 |
| WO | 2003016288 | A1 | 2/2003 |
| WO | 2008025539 | A1 | 3/2008 |
| WO | 2008025540 | A1 | 3/2008 |
| WO | 2011020615 | A1 | 2/2011 |
| WO | 2013007387 | A1 | 1/2013 |
| WO | 2013071169 | A1 | 5/2013 |
| WO | 2014182943 | A1 | 11/2014 |
| WO | 2014182945 | A1 | 11/2014 |
| WO | 2014182950 |    | 11/2014 |
| WO | 2014182951 | A1 | 11/2014 |
| WO | 2016049069 | A1 | 3/2016 |
| WO | 2016096115 | A1 | 6/2016 |
| WO | 2016096116 | A1 | 6/2016 |
| WO | 2016112305 | A1 | 7/2016 |
| WO | 2017075056 | A1 | 5/2017 |
| WO | 2017091600 |    | 6/2017 |
| WO | 2017091602 |    | 6/2017 |
| WO | 2017091617 | A1 | 6/2017 |
| WO | 2017091627 | A1 | 6/2017 |
| WO | 2017151816 | A1 | 9/2017 |
| WO | 17205684   | A1 | 11/2017 |
| WO | 2017210526 | A1 | 12/2017 |
| WO | 2017218330 | A1 | 12/2017 |
| WO | 2017218337 | A1 | 12/2017 |
| WO | 2017218379 | A1 | 12/2017 |

(Continued)

OTHER PUBLICATIONS

Bifari et al (Pharmacological Research, 2018, 137, 219-229) (Year: 2018).*
O'Neil et al (The Lancet, Aug. 25, 2018, 392, 637-649) (Year: 2018).*
Lau et al (Journal of Medicinal Chemistry, 2015, 58, 7370-7380) (Year: 2015).*
Knudsen et al (Frontiers in Endocrinology, Apr. 2019, vol. 10, Article 155, 1-32). (Year: 2019).*
Armstrong et al., "Liraglutide safety and efficacy in patients with non-alcoholic steatohepatitis (LEAn); a multicentre, double-blind, randomised, placebo-controlled phase 2 study." The Lancet, Feb. 2016, vol. 387, No. 10019, pp. 679-690.

(Continued)

*Primary Examiner* — Sudhakar Katakam
(74) *Attorney, Agent, or Firm* — Leon Y. Lum

(57) ABSTRACT

The present invention is directed to use of the GLP-1 receptor agonist semaglutide in medical therapy for the treatment of non-alcoholic steatohepatitis.

16 Claims, 2 Drawing Sheets

(56) References Cited

FOREIGN PATENT DOCUMENTS

| WO | 18071528 A1 | 4/2018 |
| WO | 2018064373 A1 | 4/2018 |
| WO | 2018089212 | 5/2018 |
| WO | 2018138352 A1 | 8/2018 |
| WO | 2018161022 A1 | 9/2018 |
| WO | 2018167194 | 9/2018 |
| WO | 2018183193 A1 | 10/2018 |
| WO | 2018183342 | 10/2018 |
| WO | 2018191393 A1 | 10/2018 |
| WO | 2018193006 A1 | 10/2018 |
| WO | 18223073 A1 | 12/2018 |
| WO | 2018231851 A1 | 12/2018 |
| WO | 19018610 A1 | 1/2019 |
| WO | 2019030268 A1 | 2/2019 |
| WO | 2019071216 | 4/2019 |
| WO | 19143767 A1 | 7/2019 |
| WO | 2019164799 A1 | 8/2019 |
| WO | 19173505 A1 | 9/2019 |
| WO | 19199642 A1 | 10/2019 |
| WO | 2019209738 A1 | 10/2019 |
| WO | 19213611 A1 | 11/2019 |
| WO | 2019211451 | 11/2019 |
| WO | 2020084126 A1 | 4/2020 |
| WO | 2020102337 A1 | 5/2020 |
| WO | 2020102351 A1 | 5/2020 |
| WO | 2020150136 | 7/2020 |
| WO | 2020172075 | 8/2020 |
| WO | 2020185686 A1 | 9/2020 |

OTHER PUBLICATIONS

Brunt et al., "Histopathology of nonalcoholic fatty liver disease." World Journal of Gastroenterology, Nov. 2010, vol. 16, No. 42, pp. 5286-5296.

Diehl et al., "Cause, pathogenesis, and treatment of nonalcoholic steatohepatitis." New England Journal of Medicine, Nov. 2017, vol. 377, No. 21, pp. 2063-2072.

Estes et al.,"Modeling the epidemic of nonalcoholic fatty liver disease demonstrates an exponential increase in burden of disease." Hepatology, Jan. 2018, vol. 67, No. 1, pp. 123-133.

Kleiner et al., "Design and validation of a histological scoring system for nonalcoholic fatty liver disease." Hepatology, Jun. 2005, vol. 41, No. 6, pp. 1313-1321.

Newsome et al., "Effect of semaglutide on liver enzymes and markers of inflammation in subjects with type 2 diabetes and/or obesity." Alimentary pharmacology & therapeutics, Jun. 2019, vol. 50, No. 2, pp. 193-203.

Oseini et al., "Therapies in non-alcoholic steatohepatitis (NASH)." Liver international, Jan. 2017, vol. 37, pp. 97-103.

Ranjbar et al., "Effects of newer antidiabetic drugs on nonalcoholic fatty liver and steatohepatitis: think out of the box." Metabolism, Dec. 2019, vol. 101, No. 154001, p. 1-12.

Sumida et al., "Antidiabetic therapy in the treatment of nonalcoholic steatohepatitis." International Journal of Molecular Sciences, Mar. 2020, vol. 21, No. 6, p. 1-22.

Sumida et al., "Current and future pharmacological therapies for NAFLD/NASH." Journal of gastroenterology, Mar. 2018, vol. 53, No. 3, pp. 362-376.

"Altimmune Announces Data Presentation on ALT-801, its Balanced and Long-Acting GLP-1/Glucagon Receptor Dual Agonist for NASH, at the Digital International Liver Congress™ 2020," Altimmune, Inc., Aug. 26, 2020, 4 pages.

"Clinical Trial: Study of Semaglutide for Non-Alcoholic Fatty Liver Disease (NAFLD), a Metabolic Syndrome With Insulin Resistance, Increased Hepatic Lipids, and Increased Cardiovascular Disease Risk (The Slim Liver Study)," US Fed News, Jan. 3, 2020, 2 pages.

"National Institute of Diabetes and Digestive and Kidney Diseases (NIDDK) Listed a New Clinical Trial for NonAlcoholic Fatty Liver Disease, the HEpatic Response to Oral Glucose, and the Effect of Semaglutide (NAFLD HEROES)," Athena Information Solutions Ltd., Contify Life Science News, Mar. 21, 2019, 2 pages.

"Novo Nordisk in-licences potential NASH candidate from Japan," The Pharma Letter, Nov. 7, 2019, 2 pages.

"Novo Nordisk submits diabetes pill for U.S. approval," Reuters, Mar. 20, 2019, 10 pages.

"Novo Nordisk trumpets NASH data with semaglutide," PMLive.com—News, May 7, 2020, 2 pages.

"Novo Nordisk's Next Crown Jewel," Source: Seeking Alpha, Aug. 21, 2017.

"Novo-direktør: Semaglutid har potentiale uden for diabetes, MedWatch DK, Mar. 8, 2018, 3 pages".

"POXEL announces program update and preclinical results on PXL770 for NASH combinations and other metabolic diseases," Business Wire, May 25, 2020, 5 pages.

"Progress on NASH treatments, but no home run yet," ConscienHealth, Nov. 20, 2020, 1 page.

"Spitfire Pharma's SP-1373 outscored semaglutide and elafibranor in a biopsy-proven translational mouse model of non-alcoholic steatohepatitis (NASH)," Spitfire Pharma, Inc., Jan. 4, 2018, 3 pages.

"The Race To Find A Treatment For NASH," RTTNews, Williamsville, Jan. 16, 2018, 6 pages.

Amy Brown, "Novo bids for recognition in the year of Nash," Evaluate Vantage, Mar. 4, 2020, 9 pages.

Amy Brown, "Novo's Nash play takes shape," Evaluate Vantage, May 6, 2020, 8 pages.

Angus Liu, "Novo Nordisk's diabetes med semaglutide shows promise in NASH. Can it deliver in phase 3?," Fierce Pharma, May 6, 2020, 5 pages.

Derrick et al., "A Primer on NASH," Benzinga Newswires, Southfield, Dec. 15, 2016, 2 pages.

George Underwood, "Gilead and Novo Nordisk collaborate for NASH trial," Pharma Phorum, Apr. 12, 2019, 2 pages.

Jason Mast, "Novo Nordisk quietly nabs a rare 'breakthrough' status in NASH for its cash cow," Endpoint, Oct. 30, 2020, 8 pages.

Josh Nathan-Kazis, "A Fatty Opportunity In Drugs May Wear Thin—Barron's," Dow Jones International News, Dec. 27, 2019, 4 pages.

Kenny Walter, "Semaglutide Reports Positive Data from Phase 2 NASH Trial," HCP Live, May 7, 2020, 2 pages.

Semaglutide Drug Data, Citeline, Latest Change Date Dec. 8, 2020, 22 pages.

Simon Wentworth, "Novo Nordisk CSO warns NASH market will develop slowly, urges all to 'moderate expectations'," ThePharmaLetter, Nov. 28, 2017, 4 pages.

Dhillon et al.,"Semaglutide: First Global Approval." Feb. 2018, Drugs, vol. 78, No. 2, pp. 275-284.

Katsiki et al.,"Semaglutide, lipidlowering drugs, and NAFLD" May 2017, Lancet diabetes & endocrinology, vol. 5, No. 5, p. 329.

Legry et al.,"Abstract 2198: Elafibranor synergizes with semaglutide to reduce liver steatosis in a model of NASH." Oct. 2019, Hepatology, vol. 70, No. 1, pp. 1298A.

Norlin et al.,"Absliact 2078: Semaglutide, a novel long acting GLP-1 receptor agonist, reduced features of NASH in two different diet-induced mouse models." Oct. 2017, Hepatology, vol. 66, No. 1, pp. 1096A.

Norlin et al. Abstract 2142: Semaglutide reduces hepatic inflammatory monocytes and macrophages in two preclinical NASH models, Oct. 2019, Hepatology, vol. 70, No. 1, pp. 1268A.

Sumida et al.,"Current and new pharmacotherapy options for non-alcoholic steatohepatitis." Apr. 2020, Expert Opinion on Pharmacotherapy, vol. 21, No. 8, pp. 953-967.

Rakipovski et al., "The GLP-1 Analogs Liraglutide and Semaglutide Reduce Atherosclerosis in ApoE-/- and LDLr-/- Mice by a Mechanism That Includes Inflammatory Pathways," JACC: Basic To Translational Science, Dec. 2018, vol. 3, No. 6, pp. 844-857.

"Investigation of Efficacy and Safety of Three Dose Levels of Subcutaneous Semaglutide Once Daily Versus Placebo in Subjects With Non-alcoholic Steatohepatitis," NIH, NLM, Clinical Trials.gov, NCT02970942, Nov. 22, 2016, https://clinicaltrials.gov/ct2/show/NCT02970942, accessed Sep. 7, 2021.

Piazzolla et al., "Noninvasive Diagnosis of NAFLD and NASH," Cells, Apr. 2020, vol. 9, No. 4, 1005, 17 pages.

(56) References Cited

OTHER PUBLICATIONS

Angulo et al., "Liver Fibrosis, but no Other Histologic Features, Associates with Long-term Outcomes of Patients With Nonalcoholic Fatty Liver Disease," Gastroenterology 149(2):389-97.e10 (2015).
Berge, et al., "Pharmaceutical Salts," Journal of Pharmaceutical Science 66(1):1-19 (1977).
D'Alessio, et al., "Glucagon-like peptide 1 enhanced glucose tolerance both by stimulation of insulin release and by increasing insulin-independent glucose disposal," J. Clin Invest 93(5):2236-2266 (1994).
Foster, "Deuterium Isotope Effects in Studies of Drug Metabolism," Trends Pharmacol. Sci. 5(12):524-527 (1984).
Harwood, "Treating the metabolic syndrome: acetyl-CoA carboxylase inhibition," Expert Opin Ther Targets, 9:2, 267-281 (2005).
Loomba et al. "GS-0976 Reduces Hepatic Steatosis and Fibrosis Markers in Patients with Nonalcoholic Fatty Liver Disease," Gastroenterology. 155(5):1463-1473 (2018).
Loomba et al., "Combination Therapies Including Cilofexor and Firsocostat for Bridging Fibrosis and Cirrhosis Attribuatable to NASH," Hepatology 73(2):625-643 (2020).
Loomba et al., "Multicenter validation of association between decline in MRI-PDFF and histologic response in nonalcoholic steatohepatitis," Hepatology 2020c;72(4):1219-1229.
Loomba et al., Magnetic resonance imaging-proton density fat fraction (MRIPDFF) to predict treatment response on NASH liver biopsy: a secondary analysis of the resmetirom randomized placebo-controlled phase 2 clinical trial, J Hepatol 2020d;73:S56 (AS077).
Newsome, "FibroScan-AST (FAST) score for the non-invasive identification of patients with non-alcoholic steatohepatitis with significant activity and fibrosis: a prospective derivation and global validation study," Lancet Gastroenterol Hepatol. 5(4):362-373 (2020).
Patel et al., "Cilofexor, a Nonsteroidal FXR Agonist, in Patients With Noncirrhotic NASH:A Phase 2 Randomized Controlled Trial," Hepatology 72(1):58-71 (2020).
Pellicciari et al., "6r-Ethyl-Chenodeoxycholic Acid (6-ECDCA), a Potent and Selective FXR Agonist Endowed with Anticholestatic Activity," Journal of Medicinal Chemistry 15(45):3569-72 (2002).
Sanyal et al., "The Natural History of Advanced Fibrosis Due to Nonalcoholic Steatohepatitis: Data From the Simtuzumab Trials," Hepatology 2019;70(6):1913-1927.
Sorli et al., "Efficacy and safety of once-weekly semaglutide monotherapy versus placebo in patients with type 2 diabetes (SUSTAIN 1): a double-blind, randomised, placebo-controlled, parallel-group, multinational, multicentre phase 3a trial," Lancet Diabetes Endocrinol. 2017;5(4):251-260.
Stine et al."Change in MRI-PDFF and Histologic Response in Patients With Nonalcoholic Steatohepatitis: A Systematic Review and Meta-Analysis," Clin Gastroenterol Hepatol. S1542-3565(20)31220-9 (2020).
Vali et al., "Enhanced liver fibrosis test for the non-invasive diagnosis of fibrosis in patients with NAFLD: A systematic review and meta-analysis," J. Hepatol. 73:252-262 (2020).
Vilar-Gomez, "Weight Loss Through Lifestyle Modification Significantly Reduces Features of Nonalcoholic Steatohepatitis," Gastroenterology 149(2):367-78.e5 (2015).
Wettergren et al. "Truncated GLP-1 (Proglucagon 78-107-Amide) Inhibits Gastric and Pancreatic Functions in Man," Dig Dis Sci 38(4):665-73 (1993).
Younossi et al., "Fatigue and Pruritus in Patients with Advanced Fibrosis Due to Nonalcoholic Steatohepatitis: The Impact on Patient-Reported Outcomes," 4(11):1637-1650 (2020).
Younossi et al., "Obeticholic acid for the treatment of non-alcoholic steatohepatitis: interim analysis from a multicentre, randomised, placebo-controlled phase 3 trial," Lancet 394:2184-2196 (2019).
NASH slide entitled "Novo Nordisk is investigating its opportunities within NASH" presented at ADA 2019 (1 page).
Newsome et al., "A Placebo-Controlled Trial of Subcutaneous Semaglutide in Nonalcoholic Steatohepatitis," The New England Journal of Medicine, Nov. 13, 2020, vol. 384, No. 12, 61 pages.

* cited by examiner

SEMAGLUTIDE FOR USE IN MEDICINE

CROSS-REFERENCE TO RELATED APPLICATIONS

This application claims priority to European Patent Applications 20173341.7, filed May 6, 2020 and 20171536.4, filed Apr. 27, 2020; the contents of which are incorporated herein by reference.

TECHNICAL FIELD

The present invention relates to medical therapy comprising administration of the GLP-1 receptor agonist semaglutide in non-alcoholic fatty liver disease including non-alcoholic steatohepatitis.

BACKGROUND

The condition defined as non-alcoholic fatty liver disease (NAFLD) involves excess storage of fat in the liver, also referred to as liver steatosis. Non-alcoholic steatohepatitis (NASH) is a disease falling under NAFLD that is characterised by accumulation of fat in the liver due to causes other than excessive alcohol consumption and is further characterised by inflammation and in some cases also liver fibrosis (Diehl et al. N Engl J Med 2017; 377: 2063-72). NASH can further lead to cirrhosis and increases the risk of dying from liver-related causes (Estes et al. Hepatology 2018; 67: 123-133). It is not known why NAFDL progresses to NASH in some patients. By some estimates, NASH is projected to overtake hepatitis C virus infection in the near future as the leading aetiology of end-stage liver disease that requires liver transplantation (Oseini et al. Liver Int. 2017; 37(Suppl 1): 97-103).

The GLP-1 receptor agonist liraglutide was tested in subjects with NASH (Armstrong et al. Lancet 2016; 387: 679-690). However, despite numerous attempts to develop a drug therapy to treat patients suffering from NASH, there is currently no such approved therapy available. Examples of previous attempts to develop such a therapy include clinical trials involving different compounds: BI1467335 (AOC3 inhibitor), emricasan (caspase inhibitor), selonsertib (ASK1 inhibitor), cilofexor (farnesoid X receptor), and firsocostat (acetyl-CoA carboxylase inhibitor). Thus, approved medical therapies for NASH are desired.

SUMMARY

In some embodiments the present invention relates to a method of treatment of non-alcoholic steatohepatitis (NASH) comprising administration of semaglutide to a subject.

DESCRIPTION

Figure 1:
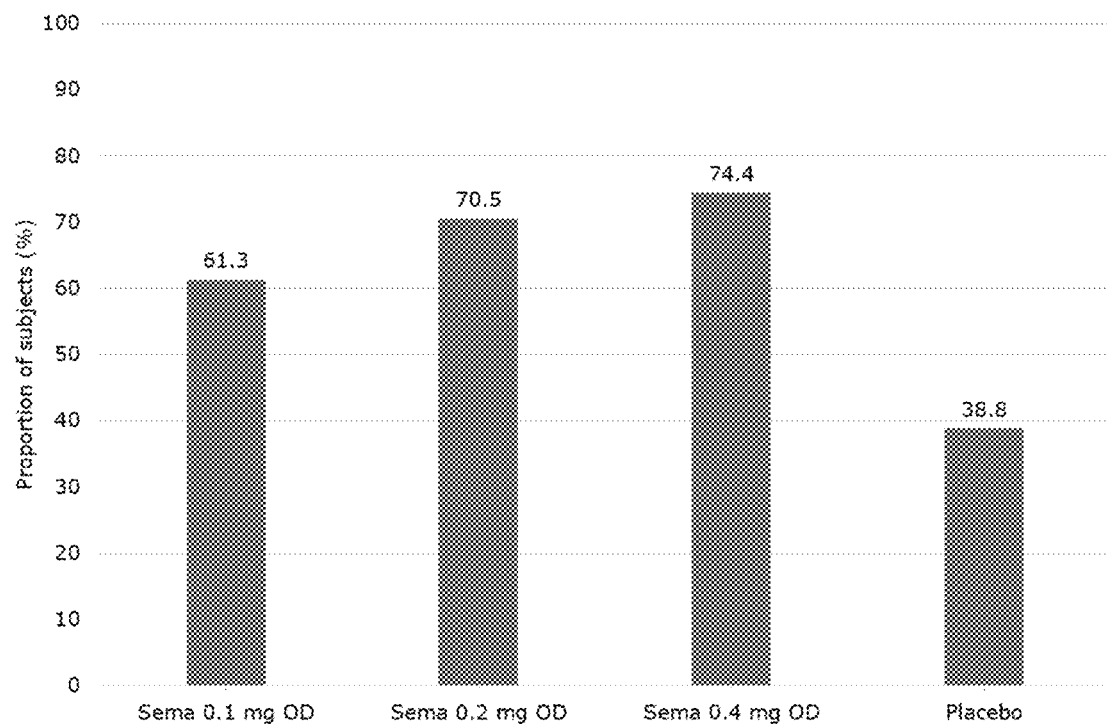
FIG. 1 shows the effect on improvement of hepatocyte ballooning at end of trial following administration of semaglutide (sema) or placebo in subjects with NASH and liver fibrosis stage 1-3 at baseline as described in Clinical Trial A herein.

The present inventors surprisingly found that administration of semaglutide markedly reduced symptoms of NASH in patients diagnosed with NASH in a clinical trial where semaglutide was administered in amounts of 0.7, 1.4 or 2.8 mg per week and compared to placebo in patients diagnosed with NASH as well as a degree of liver fibrosis within stage 1-3 according to the Kleiner fibrosis classification.

The present inventors also found that administration of semaglutide markedly reduced liver steatosis in patients diagnosed with NAFLD in a clinical trial where semaglutide was administered in an amount of 2.8 mg per week and compared to placebo in subjects diagnosed with NAFLD as well as a degree of liver steatosis and liver stiffness, and this effect increased during a continued period of treatment of at least about 48 weeks.

In some embodiments the invention relates to a method of treatment of NASH comprising administration of semaglutide to a subject. In some embodiments the invention relates to a method of treatment of NASH comprising administration of semaglutide to a subject, wherein said subject further has liver fibrosis stage 1-3 according to the Kleiner fibrosis classification. In some embodiments the invention relates to a method of treatment of NASH comprising administration of semaglutide to a subject, wherein said subject further has liver fibrosis stage 2 or 3 according to the Kleiner fibrosis classification. In some embodiments the method is for chronic management of NASH. In some embodiments the method is for chronic management of NASH. In some embodiments semaglutide is the sole GLP-1 receptor agonist administered in the methods of the invention. In some embodiments semaglutide is the sole active ingredient administered in the methods of the invention. In some embodiments semaglutide is administered by subcutaneous administration, such as in an amount in the range of about 0.7 to about 5 mg per week, such as once daily or once weekly. In some embodiments semaglutide is administered by subcutaneous administration, such as in an amount in the range of about 2.0 to about 3.5 mg per week, such as once daily or once weekly. In some embodiments semaglutide is administered by oral administration, such as in an amount in the range of about 5 to about 45 mg once daily. In some embodiments the method of the invention provides no worsening of liver fibrosis in said subject. In some embodiments the term "treatment" as used herein refers to reducing, delaying or removing the symptoms of the disease referred to. In some embodiments the term "treatment" as used herein refers to reducing or removing the symptoms of the disease referred to. In some embodiments the term "treatment" as used herein refers to reducing the symptoms of the disease referred to. In some embodiments the term "treatment" as used herein refers to delaying the symptoms of the disease referred to. In some embodiments the term "treatment" as used herein refers to removing the symptoms of the disease referred to.

A person of ordinary skill in the art will be able to determine whether a subject has NASH using routine methods, and usually involving determination based on a liver biopsy. For example, diagnosis of NASH may require (i) liver biopsy histology showing presence of steatosis, lobular inflammation, and hepatocyte ballooning, as well as (ii) no substantial alcohol consumption. In some embodiments the term "no substantial alcohol consumption" as used herein refers to consumption of no more than 20 g ethanol per day for women and no more than 30 g ethanol per day for men. If NASH progresses, a subject diagnosed with NASH may further have liver fibrosis. For simplicity, liver fibrosis may be referred to as fibrosis herein, and liver steatosis may be referred to as steatosis herein.

NASH diagnosis may further include histological evidence of NASH with an NAFLD activity score (NAS) of more than 4. In some embodiments the term "NAFLD activity score" as used herein refers to the unweighted sum of the individual scores of steatosis (score 0-3), lobular inflammation (score 0-3), and hepatocyte ballooning (score 0-2) determined by liver biopsy histology according to NASH-CRN; thus, NAS is in the range of 0 to 8. In some embodiments NASH-CRN is as published in Kleiner et al. Hepatology. 2005; 41(6):1313-21 (e.g. Table 1) and Brunt et al. World J Gastroenterol. 2010; 16(42):5286-96. In some embodiments the term "steatosis" as used herein refers to liver biopsy histology showing low- to medium-power evaluation of parenchymal involvement by steatosis and is one of the stages with a score selected from the group consisting of "0" (<5%), "1" (5%-33%), "2" (>33%-66%), and "3" (>66%) according to NASH-CRN. In some embodiments the term "lobular inflammation" as used herein refers to the overall assessment of all inflammatory foci in liver biopsy histology and is one of the stages with a score selected from the group consisting of "0" (no foci), "1" (<2 foci per 200 times magnification field), "2" (2-4 foci per 200 times magnification field) and "3" (>4 foci per 200 times magnification field) according to NASH-CRN. In some embodiments the term "hepatocyte ballooning" as used herein refers to liver biopsy histology showing one of the stages with a score selected from the group consisting of "0" (none), "1" (few balloon cells) and "2" (many cells/prominent ballooning) according to NASH-CRN.

In some embodiments the method of the invention provides an improvement of NASH. In some embodiments the term "improvement of NASH" as used herein refers to a decrease of NAFLD activity score (NAS), i.e., a decrease of at least one of the individual scores of steatosis (score 0-3), lobular inflammation (score 0-3), or hepatocyte ballooning (score 0-2) determined by liver biopsy histology according to NASH-CRN; for example, reduction from a NAS score 6 to a NAS score 5.

In some embodiments the method of the invention provides resolution of NASH. In some embodiments the term "resolution of NASH" as used herein refers to the subject no longer fulfilling the criteria for a NASH diagnosis. In some embodiments the term "resolution of NASH" refers to a liver biopsy histology showing (i) no more than mild residual inflammatory cells (i.e. inflammation score 0 or 1 according to NASH-CRN), (ii) no hepatocyte ballooning (i.e. hepatocyte ballooning score of 0 according to NASH-CRN), and (iii) any value for steatosis (i.e. steatosis score of 0-3 according to NASH-CRN). In some embodiments the method of the invention provides an improvement of lobular inflammation and/or hepatocyte ballooning. In some embodiments the term "improvement of lobular inflammation" as used herein refers to reduction by at least one stage of lobular inflammation (score 0-3) as defined herein; for example, reduction from a score 3 to a score 1. In some embodiments the term "improvement of hepatocyte ballooning" as used herein refers to reduction by at least one stage of hepatocyte ballooning (score 0-2) as defined herein; for example, reduction from a score 2 to a score 0.

In some embodiments the term "fibrosis" as used herein refers to the fibrosis stage in NASH described by the Kleiner fibrosis classification. In some embodiments the terms "Kleiner fibrosis classification" or "fibrosis stage" are used interchangeably herein and refer to the classification as defined in Kleiner et al. Hepatology, 2005; 41(6):1313-21 which consists of the stages selected from the group consisting of "0" (absence of fibrosis), "1" (portal/perisinusoidal fibrosis), "2" (perisinusoidal and portal/periportal fibrosis), "3" (septal or bridging fibrosis), and "4" (cirrhosis). In some embodiments the method of the invention provides no worsening of liver fibrosis. In some embodiments the terms "no worsening of liver fibrosis" or "no worsening of liver fibrosis stage" as used interchangeably herein refers to no increase of at least one stage of the Kleiner fibrosis classification.

In some embodiments the method of the invention reduces enhanced liver fibrosis (ELF). In some embodiments the term "enhanced liver fibrosis" (also referred to as ELF) as used herein refers to a score derived as a log-linear combination based on blood sample levels of hyaluronic acid (HA), amino-terminal propeptide of type III collagen (P3NP), and tissue inhibitor of metalloproteinase 1 (TIMP1) according to Formula (I):

$$ELF = -7.412 + 0.681 \times \ln(c_{HA}) + 0.775 \times \ln(c_{P3NP}) + 0.494 \times \ln(c_{TIMP1}) \qquad (I)$$

where $c_{HA}$ is the serum concentration of HA in ng/ml, $c_{P3NP}$ is the serum concentration of P3NP in ng/ml, and $c_{TIMP1}$ is the serum concentration of TIMP1 in ng/ml.

In some embodiments the invention relates to a method of treatment of non-alcoholic fatty liver disease (NAFLD) comprising administration of semaglutide to a subject.

The subject to be administered semaglutide according to the present invention may be human, such as an adult human (also referred to as adult).

In some embodiments the subject has liver fibrosis stage 1-3 (i.e., a liver fibrosis stage selected from the group consisting of liver fibrosis stage 1, 2, and 3), wherein the liver fibrosis may be defined according to the Kleiner fibrosis classification. In some embodiments the subject has liver fibrosis stage 2 or 3. In some embodiments the subject has liver fibrosis stage 1. In some embodiments the subject has liver fibrosis stage 2. In some embodiments the subject has liver fibrosis stage 3. The stages of liver fibrosis as referred to herein may be defined according to the Kleiner fibrosis classification.

In some embodiments the subject has one or more further indications, such as selected from the group consisting of type 2 diabetes, overweight (BMI≥27), and obesity (BMI≥30). In some embodiments the subject further suffers from overweight, obesity, hyperglycemia, type 2 diabetes, impaired glucose tolerance and/or type 1 diabetes. The term "BMI" as used herein is a measure of body fat based on height and body weight of a subject and is calculated as BMI=(body weight in kilograms)/(height in meters)$^2$. In some embodiments the subject further has type 2 diabetes. In some embodiments the subject further is overweight. In some embodiments the subject further has obesity. In some embodiments the subject has a BMI of at least 25 kg/m$^2$, such as at least 27 kg/m$^2$, at least 30 kg/m$^2$, or between 30-50 kg/m$^2$.

In some embodiments concentrations of the liver enzymes alanine aminotransferase (ALT) and aspartate aminotransferase (AST) given herein are given as the serum concentration in international units per litre (U/l).

Semaglutide

The method of the invention comprises the GLP-1 receptor agonist semaglutide. Semaglutide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8, Arg34]GLP-1-(7-37) and may be prepared as described in Example 4 of WO2006/097537. In some embodiments the term "GLP-1 receptor agonist" as used herein refers to any compound, including peptides and non-peptide compounds, which binds to the human GLP-1 receptor with a potency ($EC_{50}$) of below 100 nM as determined by methods known in the art, see for example WO98/08871. In some embodiments methods for identifying GLP-1 receptor agonists are described in WO93/19175.

Administration Regimen

In some embodiments semaglutide is be administered once daily or less frequent, such as once daily or once weekly. In some embodiments the GLP-1 receptor agonist is administered at any time in the day. In some embodiments the method of the invention is continued for at least about 48 weeks, such as at least about 1 year.

In some embodiments the method according to the invention is for chronic management of NASH. In some embodiments the term "chronic management" as used herein refers to continuing administering semaglutide according to the method of the invention for an extended period of time, such as at least 1 year or longer. In some embodiments, the term "chronic management" as used herein refers to continuing administering semaglutide according to the method of the invention for at least 5 years, such as at least 10 years or at least 20 years. In some embodiments, the term "chronic management" as used herein refers to continuing administering semaglutide according to the method of the invention for the remaining lifetime of a subject. In some embodiments the method according to the invention is continued for at least about 48 weeks. In some embodiments chronic management comprises administration of semaglutide in an amount and frequency, e.g. as specified herein, sufficient for the treatment of NASH.

In some embodiments semaglutide is the sole GLP-1 receptor agonist administered in the methods of the invention. In some embodiments semaglutide is the only active ingredient administered in the methods of the invention. In some embodiments semaglutide is the only active ingredient administered in the methods of the invention. In some embodiments the method of the invention comprises administering one or more additional active ingredients which are not GLP-1 receptor agonists to the subject.

Parenteral Administration

In some embodiments semaglutide is administered via parenteral administration. In some embodiments parenteral administration is subcutaneous administration, for example subcutaneous injection. Semaglutide may be administered using a pen-injector, such as a 3 ml disposable pen-injector.

In some embodiments semaglutide is administered in an amount of 0.5-5 mg semaglutide per week, such as 1.0-4.5 mg or 2.0-3.0 mg or semaglutide per week. In some embodiments semaglutide is administered in an amount of about 0.7-5 mg semaglutide per week, such as about 0.7-3.5 mg semaglutide per week. In some embodiments semaglutide is administered in an amount of about 2.0-4.0 mg semaglutide per week, such as about 2.0-3.5 mg or about 2.0-3.0 mg or semaglutide per week. In some embodiments semaglutide is administered in an amount of about 1.2-3.5 mg semaglutide per week, such as about 1.8-3.2 mg or about 2.4-3.0 mg or semaglutide per week. In some embodiments semaglutide is administered in an amount of about 1.4 mg, such as about 1.5 mg or about 1.6 mg, semaglutide per week. In some embodiments semaglutide is administered in an amount of about 1.7 mg, such as about 1.8 mg or about 1.9 mg, semaglutide per week. In some embodiments semaglutide is administered in an amount of about 2.0 mg, such as about 2.1 mg or about 2.2 mg, semaglutide per week. In some embodiments semaglutide is administered in an amount of about 2.3 mg, such as about 2.4 mg or about 2.5 mg, semaglutide per week. In some embodiments semaglutide is administered in an amount of about 2.6 mg, such as about 2.7 mg or about 2.8 mg, semaglutide per week. In some embodiments semaglutide is administered in an amount of about 2.9 mg, such as about 3.0 mg or about 3.1 mg, semaglutide per week. In some embodiments semaglutide is administered in an amount of about 3.2 mg, such as about 3.3 mg or about 3.4 mg, semaglutide per week.

In some embodiments semaglutide is administered via subcutaneous administration in an amount of 0.1-1 mg semaglutide once daily, such as 0.2-0.9 mg or 0.3-0.8 mg or semaglutide once daily. In some embodiments semaglutide is administered in an amount of about 0.4-0.9 mg semaglutide once daily, such as about 0.5-0.8 mg or about 0.6-0.7 mg or semaglutide once daily. In some embodiments semaglutide is administered in an amount of about 0.2 mg, such as about 0.3 mg or about 0.4 mg, semaglutide once daily. In some embodiments semaglutide is administered in an amount of about 0.5 mg, such as about 0.6 mg or about 0.7 mg, semaglutide once daily. In some embodiments semaglutide is administered in an amount of about 0.8 mg, such as about 0.9 mg or about 1.0 mg, semaglutide once daily.

In some embodiments semaglutide is administered in an amount of 0.5-5 mg semaglutide once weekly, such as 1.0-4.5 mg or 2.0-3.0 mg or semaglutide once weekly. In some embodiments semaglutide is administered in an amount of about 0.7-5 mg semaglutide once weekly, such as about 0.7-3.5 mg semaglutide once weekly. In some embodiments semaglutide is administered in an amount of about 2.0-4.0 mg semaglutide once weekly, such as about 2.0-3.5 mg or about 2.0-3.0 mg or semaglutide once weekly. In some embodiments semaglutide is administered in an amount of about 1.2-3.5 mg semaglutide once weekly, such as about 1.8-3.2 mg or about 2.4-3.0 mg or semaglutide once weekly. In some embodiments semaglutide is administered in an amount of about 1.4 mg, such as about 1.5 mg or about 1.6 mg, semaglutide once weekly. In some embodiments semaglutide is administered in an amount of about 1.7 mg, such as about 1.8 mg or about 1.9 mg, semaglutide once weekly. In some embodiments semaglutide is administered in an amount of about 2.0 mg, such as about 2.1 mg or about 2.2 mg, semaglutide once weekly. In some embodiments semaglutide is administered in an amount of about 2.3 mg, such as about 2.4 mg or about 2.5 mg, semaglutide once weekly. In some embodiments semaglutide is administered in an amount of about 2.6 mg, such as about 2.7 mg or about 2.8 mg, semaglutide once weekly. In some embodiments semaglutide is administered in an amount of about 2.9 mg, such as about 3.0 mg or about 3.1 mg, semaglutide once weekly. In some embodiments semaglutide is administered in an amount of about 3.2 mg, such as about 3.3 mg or about 3.4 mg, semaglutide once weekly.

Oral Administration

Semaglutide may be administered orally, for example in the form of a solid oral dosage form selected from the group consisting of a tablet, a coated tablet, a sachet and a capsule (such as hard or soft gelatine capsule). In some embodiments semaglutide is administered once daily via oral administration.

In some embodiments semaglutide is administered in an amount of 5-45 mg, such as 10-40 mg or 15-35 mg, via oral administration. In some embodiments semaglutide is administered in an amount of 7-44 mg, such as 12-43 mg or 18-42 mg, via oral administration. In some embodiments semaglutide is administered in an amount of 20-41 mg, such as 22-40 mg or 24-39 mg, via oral administration. In some embodiments semaglutide is administered in an amount of about 26-38 mg, such as about 28-37 mg or about 30-36 mg, via oral administration. In some embodiments semaglutide is administered in an amount of about 30 mg, such as about 31 mg or about 32 mg, via oral administration. In some embodiments semaglutide is administered in an amount of about 33 mg, such as about 34 mg or about 35 mg, via oral administration. In some embodiments semaglutide is administered in an amount of about 36 mg, such as about 37 mg or about 38 mg, via oral administration. In some embodiments semaglutide is administered in an amount of about 39 mg, such as about 40 mg or about 41 mg, via oral administration. In some embodiments semaglutide is administered in an amount of about 3, about 7 or about 14 mg, via oral administration. In some embodiments the treatment dosage for oral administration is in the range of 3-50 mg semaglutide per day, such as 10-40 mg or 15-40 mg, semaglutide per day.

Dose Escalation

Administration of semaglutide may be initiated via dose escalation, i.e. beginning with an amount lower than the treatment dosage and gradually increasing towards the treatment dosage over time. Dose escalation may help avoid one or more unwanted side effects. As used herein, the term "treatment dosage" refers to the dosage (i.e. amount and administration frequency) of semaglutide. In some embodiments the treatment dosage results in therapeutic effect in the medical indication referred to. In some embodiments the method of the invention comprises an initial step of dose escalation, wherein the subject is administered (i) a dosage of semaglutide in the range of from about one tenth to half of the treatment dosage, and then (ii) every 2-6 weeks, such as about every 4 weeks, dosage is increased by 1.5-2.5 times, such as about 2 times, until at treatment dosage. In some embodiments the method of the invention comprises an initial step of dose escalation via parenteral administration, wherein the subject is administered (i) a dosage of semaglutide in the range of 0.2-0.5 mg semaglutide per week, such as about 0.35 mg semaglutide per week, and then (ii) every 2-6 weeks, such as about every 4 weeks, dosage is increased by 1.5-2.5 times, such as about 2 times, until at treatment dosage. In some embodiments, and unless otherwise specified, amounts and/or administration frequency for semaglutide mentioned herein refer to the treatment dosage. In some embodiments the treatment dosage for subcutaneous administration is in the range of 0.5-5 mg semaglutide per week, such as 1.0-4.5 mg or 2.0-4.0 mg or semaglutide per week. In some embodiments the treatment dosage is in the range of 1.2-3.5 mg semaglutide per week, such as 1.8-3.2 mg or 2.4-3.0 mg or semaglutide per week.

Composition

In the method of the invention semaglutide may be administered in the form of a pharmaceutical composition, also referred to as a composition herein. The pharmaceutical composition may be in a liquid or solid form.

Parenteral Administration

The pharmaceutical composition may comprise semaglutide in a concentration from 0.1 mg/ml to 100 mg/ml. In some embodiments the pharmaceutical composition comprises 0.01-50 mg/ml, or 0.01-20 mg/ml, or 0.01-10 mg/ml semaglutide. In some embodiments the pharmaceutical composition comprises 0.1-20 mg/ml semaglutide.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more pharmaceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. semaglutide. The excipient may be an inert substance, an inactive substance, and/or a not medicinally active substance.

In some embodiments the pharmaceutical composition has a pH in the range of about 7.0-10.0, such as about 7.0 to about 9.5 or about 7.2 to about 9.5. In some embodiments the pharmaceutical composition has a pH in the range of 7.0-8.5, such as about 7.0 to about 7.8 or about 7.8 to about 8.2. In some embodiments the pharmaceutical composition has a pH of about 7.4. In some embodiments the pharmaceutical composition comprises a phosphate buffer, such as a sodium phosphate buffer, e.g. disodium phosphate. In some embodiments the pharmaceutical composition comprises an isotonic agent, such as propylene glycol. In some embodiments the pharmaceutical composition comprises a preservative, such as phenol.

The pharmaceutical composition may be in the form of a solution or a suspension. In some embodiments the pharmaceutical composition is aqueous composition, such as an aqueous solution or an aqueous suspension. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. An aqueous composition may comprise at least 50% w/w water, or at least 60%, 70%, 80%, or even at least 90% w/w of water.

In some embodiments semaglutide is administered in the form of a pharmaceutical composition comprising a phosphate buffer and propylene glycol. In some embodiments semaglutide is administered in the form of a pharmaceutical composition comprising about 2-15 mM phosphate buffer and about 2-25 mg/ml propylene glycol. In some embodiments semaglutide is administered in the form of a pharmaceutical composition comprising about 0.1-20 mg/ml semaglutide, about 2-15 mM phosphate buffer, about 2-25 mg/ml propylene glycol, and a pH in the range of about 7.0-9.0. In some embodiments semaglutide is administered in the form of a pharmaceutical composition comprising about 0.1-20 mg/ml semaglutide, about 2-15 mM phosphate buffer, about 2-25 mg/ml propylene glycol, about 1-18 mg/ml phenol, and a pH in the range of about 7.0-9.0. In some embodiments semaglutide is administered in the form of a pharmaceutical composition comprising about 1.0 mg/ml semaglutide, about 1.42 mg/ml disodium phosphate dihydrate, about 14.0 mg/ml propylene glycol, about 5.5 mg/ml phenol, and a pH of about 7.4. In some embodiments semaglutide is administered in the form of a pharmaceutical composition comprising about 0.5-4 mg/ml semaglutide, about 1.42 mg/ml disodium phosphate dihydrate, about 14.0 mg/ml propylene glycol, about 5.5 mg/ml phenol, and a pH of about 7.4. In some embodiments semaglutide is administered in the form of a pharmaceutical composition comprising about 0.5-1.5 mg/ml semaglutide, about 1.42 mg/ml disodium phosphate dihydrate, about 14.0 mg/ml propylene glycol, about 5.5 mg/ml phenol, and a pH of about 7.4. In some embodiments semaglutide is administered in the form of a pharmaceutical composition comprising about 1.0-3.5 mg/ml semaglutide, about 1.42 mg/ml disodium phosphate dihydrate, about 14.0 mg/ml propylene glycol, about 5.5 mg/ml phenol, and a pH of about 7.4.

Oral Administration

In the method of the invention semaglutide may be administered in the form of a solid composition via oral administration. The solid composition may be suitable for administration by the oral route, e.g. as described further herein. In some embodiments the solid composition comprises at least one pharmaceutically acceptable excipient. The term "excipient" as used herein broadly refers to any component other than the active therapeutic ingredient(s) or active pharmaceutical ingredient(s) (API(s)). The excipient may be a pharmaceutically inert substance, an inactive substance, and/or a therapeutically or medicinally inactive substance. For oral administration, the excipient may serve various purposes, e.g. as a carrier, vehicle, filler, binder, lubricant, glidant, disintegrant, flow control agent, crystallization inhibitors solubilizer, stabilizer, colouring agent, flavouring agent, surfactant, emulsifier or combinations of thereof and/or to improve administration, and/or absorption of the therapeutically active substance(s) or active pharmaceutical ingredient(s). The amount of each excipient used may vary within ranges conventional in the art. Techniques and excipients which may be used to formulate oral dosage forms are described in Handbook of Pharmaceutical Excipients, 8th edition, Sheskey et al., Eds., American Pharmaceuticals Association and the Pharmaceutical Press, publications department of the Royal Pharmaceutical Society of Great Britain (2017); and Remington: the Science and Practice of Pharmacy, 22nd edition, Remington and Allen, Eds., Pharmaceutical Press (2013). In some embodiments the excipients for oral administration may be selected from binders, such as polyvinyl pyrrolidone (povidone), etc.; fillers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, etc.; lubricants and/or glidants such as stearic acid, magnesium stearate, sodium stearylfumarate, glycerol tribehenate, etc.; flow control agents such as colloidal silica, talc, etc.; crystallization inhibitors such as Povidone, etc.; solubilizers such as Pluronic, Povidone, etc.; colouring agents, including dyes and pigments such as iron oxide red or yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

In some embodiments the solid composition comprises a binder, such as povidone; starches; celluloses and derivatives thereof, such as microcrystalline cellulose, e.g., Avicel PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be selected from the group consisting of dry binders and/or wet granulation binders. Suitable dry binders are, e.g., cellulose powder and microcrystalline cellulose, such as Avicel PH 102 and Avicel PH 200. In some embodiments the solid composition comprises Avicel, such as Aavicel PH 102. Suitable binders for wet granulation or dry granulation are corn starch, polyvinyl pyrrolidone (povidon), vinylpyrrolidone-vinylacetate copolymer (copovidone) and cellulose derivatives like hydroxymethylcellulose, hydroxyethylcellulose, hydroxypropylcellulose and hydroxyl-propylmethylcellulose. In some embodiments the solid composition comprises povidone.

In some embodiments the solid composition comprises a filler which may be selected from lactose, mannitol, erythritol, sucrose, sorbitol, calcium phosphate, such as calcium hydrogen phosphate, microcrystalline cellulose, powdered cellulose, confectioner's sugar, compressible sugar, dextrates, dextrin and dextrose. In some embodiments the solid composition comprises microcrystalline cellulose, such as Avicel PH 102 or Avicel PH 200.

In some embodiments the solid composition comprises a lubricant and/or a glidant. In some embodiments the composition comprises a lubricant and/or a glidant, such as talc, magnesium stearate, calcium stearate, zinc stearate, glyceryl behenate, glyceryl debehenate, behenoyl polyoxyl-8 glycerides, polyethylene oxide polymers, sodium lauryl sulfate, magnesium lauryl sulfate, sodium oleate, sodium stearyl fumarate, stearic acid, hydrogenated vegetable oils, silicon dioxide and/or polyethylene glycol etc. In some embodiments the solid composition comprises magnesium stearate or glyceryl debehenate (such as the product Compritol® 888 ATO).

In some embodiments the solid composition comprises a disintegrant, such as sodium starch glycolate, polacrilin potassium, sodium starch glycolate, crospovidon, croscarmellose, sodium carboxymethylcellulose or dried corn starch. The solid composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, non-ionic surfactants, and/or zwitterionic surfactants.

In some embodiments the solid composition further comprises a delivery agent or absorption enhancer is for the present invention an excipient capable of increasing the oral exposure of semaglutide. The delivery agent may be a salt of N-(8-(2-hydroxybenzoyl)amino)caprylic acid (also referred to herein as a salt of NAC), which contains the anion N-(8-(2-hydroxybenzoyl)amino)caprylate. The structural formula of N-(8-(2-hydroxybenzoyl)amino)caprylate is shown in Formula (II).

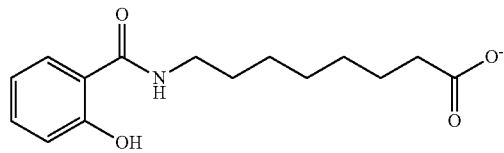

(II)

In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino) caprylic acid is selected from the group consisting of the sodium salt, potassium salt and/or calcium salt of N-(8-(2-hydroxybenzoyl)amino)caprylic acid. In some embodiments the salt of N-(8-(2-hydroxybenzoyl)amino)caprylic acid is selected from the group consisting of the sodium salt, potassium salt and/or the ammonium salt. In some embodiments the salt of N-(8-(2-hydroxybenzoyl)amino)caprylic acid is the sodium salt or the potassium salt. Salts of N-(8-(2-hydroxybenzoyl)amino)caprylate may be prepared using the method described in e.g. WO96/030036, WO00/046182, WO01/092206 or WO2008/028859. The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino)caprylic acid as well as combinations thereof. In some embodiments the delivery agent is a salt of N-(8-(2-hydroxybenzoyl)amino)caprylic acid as described in WO2007/121318. In some embodiments the delivery agent is sodium N-(8-(2-hydroxybenzoyl)amino)caprylate (referred to as "SNAC" herein), also known as sodium 8-(salicyloylamino)octanoate.

In some embodiments the composition for use in the invention is in the form of a solid composition, such as a tablet, for oral administration. In some embodiments the solid composition comprises semaglutide in an amount in the range of 0.1-50 mg, such as 0.5 to 40 mg or 1-30 mg. In some embodiments the solid composition comprises semaglutide in an amount in the range of 2-20 mg, such as 3-18 mg or 5-15 mg. In some embodiments the solid composition comprises semaglutide in an amount of about 3 mg, such as about 7 mg or about 14 mg.

In some embodiments least 30% (w/w) of the solid composition (e.g. tablet) is a salt of N-(8-(2-hydroxybenzoyl)amino)caprylic acid. In some embodiments least 50% (w/w) of the solid composition (e.g. tablet) is a salt of N-(8-(2-hydroxybenzoyl)amino)caprylic acid. In some embodiments the amount of the salt of N-(8-(2-hydroxybenzoyl)amino)caprylic acid per dose unit of the composition is in the range of 0.20-0.5 mmol, 0.25-1.0 mmol, 0.30-0.75 mmol, or such as 0.45-0.65 mmol. In some embodiments the amount of SNAC in the composition is in the range of 75-600 mg. In some embodiments the amount of SNAC in the composition is in the range of 75-400 mg, such as from 80-350 mg, such as from about 100 to about 300 mg per dose unit.

In some embodiments the solid composition comprises a lubricant, such as magnesium stearate. In some embodiments a unit dose of the solid composition comprises: 0.1-50 mg semaglutide, 25-600 mg salt of N-(8-(2-hydroxybenzoyl)amino)caprylic acid (NAC) (such as the sodium salt of NAC (SNAC)), and 0-25 mg lubricant.

In some embodiments the solid composition the solid composition is in the form of a dose unit, such as tablet. In some embodiments the weight of the unit dose is in the range of 50 mg to 1000 mg, such as in the range of 50-750 mg, or such as about 100-500 mg. In some embodiments the weight of the dose unit is in the range of 75 mg to 350 mg, such as in the range of 50-300 mg or 100-400 mg. The tablet may comprise 30% (w/w) salt of N-(8-(2-hydroxybenzoyl)amino)caprylic acid, such as the sodium salt of N-(8-(2-hydroxybenzoyl)amino)caprylic acid (SNAC). In some embodiments the composition may be granulated prior to being compressed to tablets. The composition may comprise a granular part and/or an extra-granular part, wherein the granular part has been granulated and the extra-granular part has been added after granulation. Semaglutide may be included in the granular part or the extra-granular part. In some embodiments the extra-granular part comprises semaglutide. In an embodiment the extra-granular part may further comprise a lubricant and/or a glidant. In an embodiment the granular part may comprise a lubricant and/or a glidant. In an embodiment the granular part and the extra-granular part comprise a lubricant and/or a glidant.

Unless otherwise stated, ranges herein include their end points. In some embodiments the term "a" means "one or more". In some embodiments, and unless otherwise indicated herein, terms presented in singular form also include the plural situation. Herein the term "about" means±10% of the value referred to, and includes the value. In some embodiments the term "comprise" as used herein includes "consist of". In some embodiments, pH values referred to herein are measured at 25° C.

NON-LIMITING EMBODIMENTS OF THE INVENTION

The invention is further described by the following non-limiting embodiments:

1. A method of treatment of non-alcoholic steatohepatitis (NASH) comprising administration of semaglutide to a subject.
2. The method according to any one of the preceding embodiments, wherein said method provides no worsening of liver fibrosis in said subject.
3. The method according to any one of the preceding embodiments, wherein said method reduces enhanced liver fibrosis (ELF).
4. The method according to any one of the preceding embodiments, wherein ELF is defined by Formula (I) herein.
5. A method of treatment of non-alcoholic fatty liver disease (NAFLD) comprising administration of semaglutide to a subject.
6. The method according to any one of the preceding embodiments, wherein said subject is human.
7. The method according to any one of the preceding embodiments, wherein said subject is an adult.
8. The method according to any one of the preceding embodiments, wherein said subject further has liver fibrosis stage 1-3.
9. The method according to any one of the preceding embodiments, wherein said subject further has liver fibrosis stage 2 or 3.
10. The method according to any one of the preceding embodiments, wherein said liver fibrosis is defined according to the Kleiner fibrosis classification.
11. The method according to any one of the preceding embodiments, wherein said subject further has liver fibrosis stage 1-3 according to the Kleiner fibrosis classification.
12. The method according to any one of the preceding embodiments, wherein said subject further has liver fibrosis stage 2 or 3 according to the Kleiner fibrosis classification.
13. The method according to any one of the preceding embodiments, wherein said method is for chronic management of NASH.
14. The method according to any one of the preceding embodiments, wherein said method is continued for at least about 1 year.
15. The method according to any one of the preceding embodiments, wherein said method is continued for at least about 48 weeks.
16. The method according to any one of the preceding embodiments, wherein said semaglutide is the sole active ingredient administered to said subject.
17. The method according to any one of the preceding embodiments, wherein said semaglutide is the sole GLP-1 receptor agonist administered to said subject.

18. The method according to any one of the preceding embodiments, wherein said subject is administered one or more additional active ingredients which are not GLP-1 receptor agonists.
19. The method according to any one of the preceding embodiments, wherein said semaglutide is administered by parenteral administration.
20. The method according to any one of the preceding embodiments, wherein said semaglutide is administered by subcutaneous administration.
21. The method according to any one of the preceding embodiments, wherein said semaglutide is administered in an amount in the range of about 0.7 to about 5 mg per week.
22. The method according to any one of the preceding embodiments, wherein said semaglutide is administered in an amount in the range of about 0.7 to about 3.5 mg per week.
23. The method according to any one of the preceding embodiments, wherein said semaglutide is administered in an amount in the range of about 2.0 to about 4.0 mg per week.
24. The method according to any one of the preceding embodiments, wherein said semaglutide is administered in an amount in the range of about 2.0 to about 3.5 mg per week.
25. The method according to any one of the preceding embodiments, wherein said semaglutide is administered in an amount in the range of about 2.0 to about 3.0 mg per week.
26. The method according to any one of the preceding embodiments, wherein said semaglutide is administered in an amount in of about 2.4 mg per week.
27. The method according to any one of the preceding embodiments, wherein said semaglutide is administered in an amount in of about 2.6 mg per week.
28. The method according to any one of the preceding embodiments, wherein said semaglutide is administered in an amount in of about 2.8 mg per week.
29. The method according to any one of the preceding embodiments, wherein said semaglutide is administered in an amount in of about 3.0 mg per week.
30. The method according to any one of the preceding embodiments, wherein said semaglutide is administered once daily or less frequent.
31. The method according to any one of the preceding embodiments, wherein said semaglutide is administered once daily.
32. The method according to any one of the preceding embodiments, wherein said semaglutide is administered once weekly.
33. The method according to any one of the preceding embodiments, wherein said semaglutide is administered in the form of a pharmaceutical composition comprising one or more pharmaceutically acceptable excipients.
34. The method according to any one of the preceding embodiments, wherein said semaglutide is the sole active ingredient in said pharmaceutical composition.
35. The method according to any one of the preceding embodiments, wherein said pharmaceutical composition comprises one or more additional active ingredients which are not GLP-1 receptor agonists.
36. The method according to any one of the preceding embodiments, wherein said pharmaceutical composition is in the form of an aqueous solution.
37. The method according to any one of the preceding embodiments, wherein said pharmaceutical composition comprises 0.5-5.0 mg/ml semaglutide.
38. The method according to any one of the preceding embodiments, wherein said pharmaceutical composition has a pH in the range of about 7.2 to about 7.6, such as about 7.4.
39. The method according to any one of the preceding embodiments, wherein said pharmaceutical composition further comprises a phosphate buffer and propylene glycol.
40. The method according to any one of the preceding embodiments, wherein said pharmaceutical composition further comprises about 2-15 mM phosphate buffer and about 2-25 mg/ml propylene glycol.
41. The method according to any one of the preceding embodiments, wherein said pharmaceutical composition is an aqueous solution comprising about 1.0 mg/ml semaglutide, about 1.42 mg/ml disodium hydrogen phosphate dihydrate, about 14.0 mg/ml propylene glycol, about 5.50 mg/ml phenol at about pH 7.4.
42. The method according to any one of the preceding embodiments, wherein said semaglutide is administered by oral administration.
43. The method according to any one of the preceding embodiments, wherein said semaglutide is administered once daily by oral administration.
44. The method according to any one of the preceding embodiments, wherein said semaglutide is administered in an amount of 5-45 mg semaglutide once daily by oral administration.
45. The method according to any one of the preceding embodiments, wherein said semaglutide is administered by oral administration in the form of a tablet.
46. The method according to any one of the preceding embodiments, wherein said semaglutide is administered by oral administration in the form of a solid composition, such as a tablet.
47. The method according to any one of the preceding embodiments, wherein said semaglutide is administered by oral administration in the form of a solid composition comprising SNAC, such as at least 30% (w/w) SNAC.

EXAMPLES

Methods

Clinical Trial A

A 72-week, randomised, double-blind, placebo-controlled, six-armed, parallel group, multicentre, multi-national phase 2 trial comparing once daily (OD) administration of semaglutide in three different doses (0.1 mg, 0.2 mg and 0.4 mg) with placebo in subjects with NASH was carried out. A total of 319 subjects received trial product, 302 subjects completed the trial, and 277 subjects had liver biopsy at trial week 72. Subjects received once daily (a) semaglutide of (i) 0.05 mg for 4 weeks and 0.1 mg for the remaining trial period, (ii) 0.05 mg for 4 weeks, 0.1 mg for 4 weeks, and 0.2 mg for the remaining trial period, (iii) 0.05 mg for 4 weeks, 0.1 mg for 4 weeks, 0.2 mg for 4 weeks, 0.3 mg for 4 weeks, and 0.4 mg for the remaining trial period, or (b) placebo in injection volumes corresponding to (i), (ii) or (iii). Administration was performed via subcutaneous injection using (a) an aqueous solution comprising 1.0 mg/ml semaglutide, 1.42 mg/ml disodium hydrogen phosphate dihydrate, 14.0 mg/ml propylene glycol, 5.50 mg/ml phenol at pH 7.4, or (b) a placebo solution comprising the same ingredients as (a) except no semaglutide. Inclusion criteria for subjects in the trial comprised (i) histologic evidence of NASH based on evaluation of a liver biopsy obtained up to 21 weeks before screening, (ii) a histological NAS >4 with a score of 1 or more in each sub-component of the score, and (iii) liver fibrosis stage 1, 2 or 3 according to the NASH-CRN. Screening was carried out prior to baseline in order to make assessments used to determine subject eligibility. Exclusion criteria for subjects in the trial comprised (i) documented causes of chronic liver disease other than NASH and (ii) no substantial alcohol consumption, defined in the trial as no more than 20 g ethanol per day for women or no more than 30 g ethanol per day for men. Baseline characteristics for all randomised subjects in the trial were as shown in Table A. The term "baseline" as used herein refers to the beginning of the trial prior to administration of semaglutide or placebo. The term "end of trial" as used herein in relation to Clinical Trial A refers to trial week 72. The term "all randomised subjects" as used herein refers to subjects allocated to receive semaglutide or placebo in a clinical trial. The fibrosis stage was determined according to the Kleiner fibrosis classification.

TABLE A

| | Baseline characteristics based on all randomised subjects | | | | |
|---|---|---|---|---|---|
| | Semaglutide OD | | | | |
| | 0.1 mg | 0.2 mg | 0.4 mg | Placebo | Total |
| Number of subjects | 80 | 78 | 82 | 80 | 320 |
| Age (years) [mean (SD)] | 55.2 (10.9) | 58.1 (9.9) | 54.3 (10.2) | 52.4 (10.8) | 55.0 (10.6) |
| Sex [N (%)] | | | | | |
| Female | 51 (63.8) | 52 (66.7) | 47 (57.3) | 44 (55.0) | 194 (60.6) |
| Male | 29 (36.3) | 26 (33.3) | 35 (42.7) | 36 (45.0) | 126 (39.4) |
| Region [N (%)] | | | | | |
| Europe | 44 (55.0) | 42 (53.8) | 41 (50.0) | 36 (45.0) | 163 (50.9) |
| North America | 26 (32.5) | 27 (34.6) | 29 (35.4) | 34 (42.5) | 116 (36.3) |
| Japan | 10 (12.5) | 9 (11.5) | 12 (14.6) | 10 (12.5) | 41 (12.8) |
| Type 2 diabetes [N (%)] | 49 (61.3) | 51 (65.4) | 49 (59.8) | 50 (62.5) | 199 (62.2) |
| Body weight (kg) [mean (SD)] | 98.4 (21.1) | 97.1 (22.0) | 96.6 (20.1) | 101.3 (23.3) | 98.4 (21.7) |
| BMI (kg/m$^2$) [N (%)] | | | | | |
| <25 | 1 (1.3) | 0 (0.0) | 2 (2.4) | 1 (1.3) | 4 (1.3) |
| ≥25 to <30 | 15 (18.8) | 18 (23.1) | 17 (20.7) | 14 (17.5) | 64 (20.0) |
| ≥30 to <35 | 20 (25.0) | 21 (26.9) | 25 (30.5) | 21 (26.3) | 87 (27.2) |
| ≥35 | 44 (55.0) | 39 (50.0) | 38 (46.3) | 44 (55.0) | 165 (51.6) |
| Fibrosis stage (0-4) [N (%)] | | | | | |
| 0 | 0 | 0 | 0 | 0 | 0 |
| 1 | 23 (28.8) | 19 (24.4) | 26 (31.7) | 22 (27.5) | 90 (28.1) |
| 2 | 18 (22.5) | 18 (23.1) | 14 (17.1) | 22 (27.5) | 72 (22.5) |
| 3 | 39 (48.8) | 41 (52.6) | 42 (51.2) | 36 (45.0) | 158 (49.4) |
| 4 | 0 | 0 | 0 | 0 | 0 |
| Hepatocyte ballooning (0-2) [N (%)] | | | | | |
| 0 | 0 | 0 | 0 | 0 | 0 |
| 1 | 58 (72.5) | 47 (60.3) | 55 (67.1) | 58 (72.5) | 218 (68.1) |
| 2 | 22 (27.5) | 31 (39.7) | 27 (32.9) | 22 (27.5) | 102 (31.9) |
| Lobular inflammation (0-3) [N (%)] | | | | | |
| 0 | 0 | 0 | 0 | 0 | 0 |
| 1 | 30 (37.5) | 32 (41.0) | 40 (48.8) | 33 (41.3) | 135 (42.2) |
| 2 | 47 (58.8) | 44 (56.4) | 37 (45.1) | 46 (57.5) | 174 (54.4) |
| 3 | 3 (3.8) | 2 (2.6) | 5 (6.1) | 1 (1.3) | 11 (3.4) |
| Steatosis (0-3) [N (%)] | | | | | |
| 0 | 0 | 0 | 0 | 0 | 0 |
| 1 | 21 (26.3) | 21 (26.9) | 31 (37.8) | 17 (21.3) | 90 (28.1) |
| 2 | 42 (52.5) | 43 (55.1) | 31 (37.8) | 46 (57.5) | 162 (50.6) |
| 3 | 17 (21.3) | 14 (17.9) | 20 (24.4) | 17 (21.3) | 68 (21.3) |
| Total NAFLD activity score (0-8) [mean (SD)] | 4.9 (0.8) | 4.9 (0.9) | 4.8 (0.9) | 4.9 (0.9) | 4.9 (0.9) |
| Biomarkers [mean (SD)] | | | | | |
| ELF | 9.8 (1.0) | 9.8 (0.9) | 9.9 (1.0) | 9.6 (0.9) | 9.8 (0.9) |

TABLE A-continued

| | Baseline characteristics based on all randomised subjects | | | | |
|---|---|---|---|---|---|
| | Semaglutide OD | | | | |
| | 0.1 mg | 0.2 mg | 0.4 mg | Placebo | Total |
| | Liver enzymes [geom. mean (CV)] | | | | |
| ALT (U/L) | 55 (90.4) | 53 (78.4) | 54 (83.8) | 55 (91.7) | 54 (86.2) |
| AST (U/L) | 44 (81.9) | 43 (72.9) | 44 (77.7) | 42 (83.2) | 43 (78.9) |

OD: Once daily,
N: Number of subjects,
%: Percentage of subjects,
SD: Standard deviation,
Geom.: Geometric,
CV: Coefficient of variation,
ALT: Alanine aminotransferase,
AST: Aspartate aminotransferase.

Clinical Trial B

A randomised, double-blind, placebo-controlled, parallel group, multi-centre phase 1 trial was carried out to investigate the effect of 0.4 mg semaglutide once-daily (OD) in 67 subjects with NAFLD and increased liver stiffness. Subjects received once daily either (i) semaglutide of 0.05 mg for 4 weeks, 0.1 mg for 4 weeks, 0.2 mg for 4 weeks, 0.3 mg for 4 weeks, and then 0.4 mg for the remaining trial period, or (ii) placebo in injection volumes corresponding to (i). Administration was performed via subcutaneous injection using (a) an aqueous solution comprising 1.0 mg/ml semaglutide, 1.42 mg/ml disodium hydrogen phosphate dihydrate, 14.0 mg/ml propylene glycol, 5.50 mg/ml phenol at pH 7.4, or (b) a placebo solution comprising the same ingredients as (a) except no semaglutide. Inclusion criteria for subjects in the trial comprised (i) liver steatosis of at least 10% measured by magnetic resonance imaging proton density fat fraction (MRI-PDFF) at screening, (ii) liver stiffness between 2.50 and 4.63 kPa (both inclusive) measured by magnetic resonance elastography at screening, (iii) BMI between 25.0 and 40.0 kg/m$^2$ (both inclusive) at screening, (iv) liver stiffness >6.50 kPa measured via Fibroscan® (manufactured by Echosens, Paris, France) at screening, and (v) for subjects with type 2 diabetes mellitus only, diagnosis of type 2 diabetes mellitus was at least 180 days prior to screening and with HbA1c of no more than 9.5% at screening. Screening was carried out prior to baseline in order to make assessments used to determine subject eligibility. Exclusion criteria for subjects in the trial comprised (i) documented causes of chronic liver disease other than NAFLD including NASH and (ii) no substantial alcohol consumption, defined in the trial as no more than 20 g ethanol per day for women or no more than 30 g ethanol per day for men. Baseline characteristics for all randomised subjects in the trial were shown in Table B. MRI-PDFF is a determination of the percentage of fat in the entire liver and the method is described in e.g. Caussy et al. Hepatology. 2018 August; 68(2):763-772.

TABLE B

| | Baseline characteristics based on all randomised subjects | | |
|---|---|---|---|
| | Semaglutide 0.4 mg OD | Placebo | Total |
| Number of subjects | 34 | 33 | 67 |
| Age (years) [mean (SD)] | 59.5 (10.1) | 60.5 (8.5) | 60.0 (9.3) |
| Sex [N (%)] | | | |
| Female | 11 (32.4) | 9 (27.3) | 20 (29.9) |
| Male | 23 (67.6) | 24 (72.7) | 47 (70.1) |
| Type 2 diabetes [N (%)] | 28 (82.4) | 21 (63.6) | 49 (73.1) |
| Body weight (kg) [mean (SD)] | 105.1 (15.3) | 102.3 (12.7) | 103.7 (14.0) |
| BMI group (kg/m$^2$) [N (%)] | | | |
| ≥25 to <30 | 2 (5.9) | 2 (6.1) | 4 (6.0) |
| ≥30 to <35 | 15 (44.1) | 21 (63.6) | 36 (53.7) |
| ≥35 | 17 (50.0) | 10 (30.3) | 27 (40.3) |
| Liver stiffness strata [N (%)] | | | |
| Low (<3.64 kPa) | 28 (82.4) | 29 (87.9) | 57 (85.1) |
| High (≥3.64 kPa) | 6 (17.6) | 4 (12.1) | 10 (14.9) |
| MR scan [geom. mean (CV)] | | | |
| Liver stiffness by MRE (kPa) | 3.08 (39.6) | 2.95 (38.7) | 3.02 (39.3) |
| Liver steatosis by MRI-PDFF (%) | 18.1 (70.3) | 17.3 (67.8) | 17.7 (68.9) |
| Biomarkers [mean (SD)] | | | |
| ELF | 9.2 (0.6) | 9.0 (0.7) | 9.1 (0.6) |

TABLE B-continued

Baseline characteristics based on all randomised subjects

| | Semaglutide 0.4 mg OD | Placebo | Total |
|---|---|---|---|
| Liver enzymes [geom. mean (CV)] | | | |
| ALT (U/L) | 40 (89.2) | 35 (78.1) | 37 (84.1) |
| AST (U/L) | 31 (71.5) | 29 (62.8) | 30 (67.6) |

N: Number of subjects,
%: Percentage of subjects,
SD: Standard deviation,
CV: Coefficient of variation,
MRE: Magnetic resonance elastography,
MRI-PDFF: magnetic resonance imaging proton density fat fraction,
ALT: Alanine aminotransferase,
AST: Aspartate aminotransferase.

Results

Results from Clinical Trial A

Results from Clinical Trial A described above are shown in Tables 1-6 below.

TABLE 1

Improvement of hepatocyte ballooning at end of trial compared to baseline, given as proportion of subjects (%)

| | Semaglutide OD | | | |
|---|---|---|---|---|
| Trial population | 0.1 mg | 0.2 mg | 0.4 mg | Placebo |
| Fibrosis stage 1-3 at baseline* | 61.3 | 70.5 | 74.4 | 38.8 |
| Fibrosis stage 2 or 3 at baseline | 61.4 | 66.1 | 82.1 | 39.7 |
| Fibrosis stage 1 at baseline | 60.9 | 84.2 | 57.7 | 36.4 |
| Fibrosis stage 2 at baseline | 66.7 | 72.2 | 78.6 | 40.9 |
| Fibrosis stage 3 at baseline | 59.0 | 63.4 | 83.3 | 38.9 |

*i.e. all randomised subjects

TABLE 2

Improvement of lobular inflammation at end of trial compared to baseline, given as proportion of subjects (%)

| | Semaglutide OD | | | |
|---|---|---|---|---|
| Trial population | 0.1 mg | 0.2 mg | 0.4 mg | Placebo |
| Fibrosis stage 1-3 at baseline* | 41.3 | 47.4 | 37.8 | 26.3 |
| Fibrosis stage 2 or 3 at baseline | 43.9 | 49.2 | 48.2 | 34.5 |
| Fibrosis stage 1 at baseline | 34.8 | 42.1 | 15.4 | 4.5 |
| Fibrosis stage 2 at baseline | 33.3 | 38.9 | 50.0 | 18.2 |
| Fibrosis stage 3 at baseline | 48.7 | 53.7 | 47.6 | 44.4 |

*i.e. all randomised subjects

TABLE 3

Improvement of steatosis at end of trial compared to baseline, given as proportion of subjects (%)

| | Semaglutide OD | | | |
|---|---|---|---|---|
| Trial population | 0.1 mg | 0.2 mg | 0.4 mg | Placebo |
| Fibrosis stage 1-3 at baseline* | 52.5 | 60.3 | 63.4 | 26.3 |
| Fibrosis stage 2 or 3 at baseline | 50.9 | 59.3 | 67.9 | 25.9 |
| Fibrosis stage 1 at baseline | 56.5 | 63.2 | 53.8 | 27.3 |
| Fibrosis stage 2 at baseline | 61.1 | 66.7 | 71.4 | 31.8 |
| Fibrosis stage 3 at baseline | 46.2 | 56.1 | 66.7 | 22.2 |

*i.e. all randomised subjects

The results in Tables 1-3 show that treatment with semaglutide resulted in histological resolution of non-alcoholic steatohepatitis in patients with NASH since all of the components, and in particular lobular inflammation and hepatocyte ballooning, were improved. These results also show that improvement or resolution of NASH was achieved by significantly more subjects compared to placebo for all tested semaglutide dosages based on all randomised subjects. FIG. 1 also shows the results on improvement of hepatocyte ballooning at end of trial compared to baseline based on all randomised subjects. The results in Tables 1-3 also show significant improvement of NASH compared to placebo for the 0.4 mg once daily semaglutide dosage, and in particular for subjects with fibrosis stage 1-3, fibrosis stage 2 or 3, fibrosis stage 2, or fibrosis stage 3.

TABLE 4A

Resolution of NASH at end of trial, given as proportion of subjects (%)

| | Semaglutide OD | | | |
|---|---|---|---|---|
| Trial population | 0.1 mg | 0.2 mg | 0.4 mg | Placebo |
| Fibrosis stage 1-3 at baseline* | 47.5 | 46.2 | 61.0 | 21.3 |
| Fibrosis stage 2 or 3 at baseline | 42.1 | 39.0 | 64.3 | 19.0 |
| Fibrosis stage 1 at baseline | 60.9 | 68.4 | 53.8 | 27.3 |
| Fibrosis stage 2 at baseline | 55.6 | 61.1 | 78.6 | 22.7 |
| Fibrosis stage 3 at baseline | 35.9 | 29.3 | 59.5 | 16.7 |

*i.e. all randomised subjects. Data are based on all randomised subjects with all available assessments included regardless of treatment status. Subjects with missing data are handled as non-responders.

The results in Table 4A show that treatment with semaglutide resulted in histological resolution of non-alcoholic steatohepatitis in patients with NASH and fibrosis stage 1-3 or NASH and fibrosis stage 2-3. Resolution of NASH was achieved by significantly more subjects compared to placebo for all tested semaglutide dosages based on subjects with liver fibrosis stage 1-3 at baseline. Resolution of NASH was achieved by significantly more subjects compared to placebo for all tested semaglutide dosages based on subjects with fibrosis stage 2 or 3. Resolution of NASH was achieved by significantly more subjects compared to placebo for all tested semaglutide dosages based on subjects with fibrosis stage 1, fibrosis stage 2, or fibrosis stage 3. The results in Table 4A also show significant improvement of resolution of NASH and no worsening in liver fibrosis compared to placebo for the 0.4 mg once daily semaglutide dosage, and in particular for subjects with fibrosis stage 1-3, fibrosis stage 2 or 3, fibrosis stage 2, or fibrosis stage 3.

TABLE 4B

Resolution of NASH and no worsening in liver fibrosis at end of trial,
given as proportion of subjects [% (P value relative to placebo)]

| Trial population | Semaglutide OD | | | Placebo |
|---|---|---|---|---|
| | 0.1 mg | 0.2 mg | 0.4 mg | |
| Fibrosis stage 1-3 at baseline* | 43.8 (0.0023) | 38.5 (0.0138) | 56.1 (<0.0001) | 20.0 |
| Fibrosis stage 2 or 3 at baseline | 40.4 (0.0100) | 35.6 (0.0359) | 58.9 (<0.0001) | 17.2 |
| Fibrosis stage 1 at baseline | 52.2 | 47.4 | 50.0 | 27.3 |
| Fibrosis stage 2 at baseline | 55.6 | 55.6 | 64.3 | 18.2 |
| Fibrosis stage 3 at baseline | 33.3 | 26.8 | 75.1 | 16.7 |

*i.e. all randomised subjects. Data are based on all randomised subjects with all available assessments included regardless of treatment status. Two-sided p-values are from a Cochran-Mantel-Haenszel test. Subjects with missing data are handled as non-responders.

Figure 2:
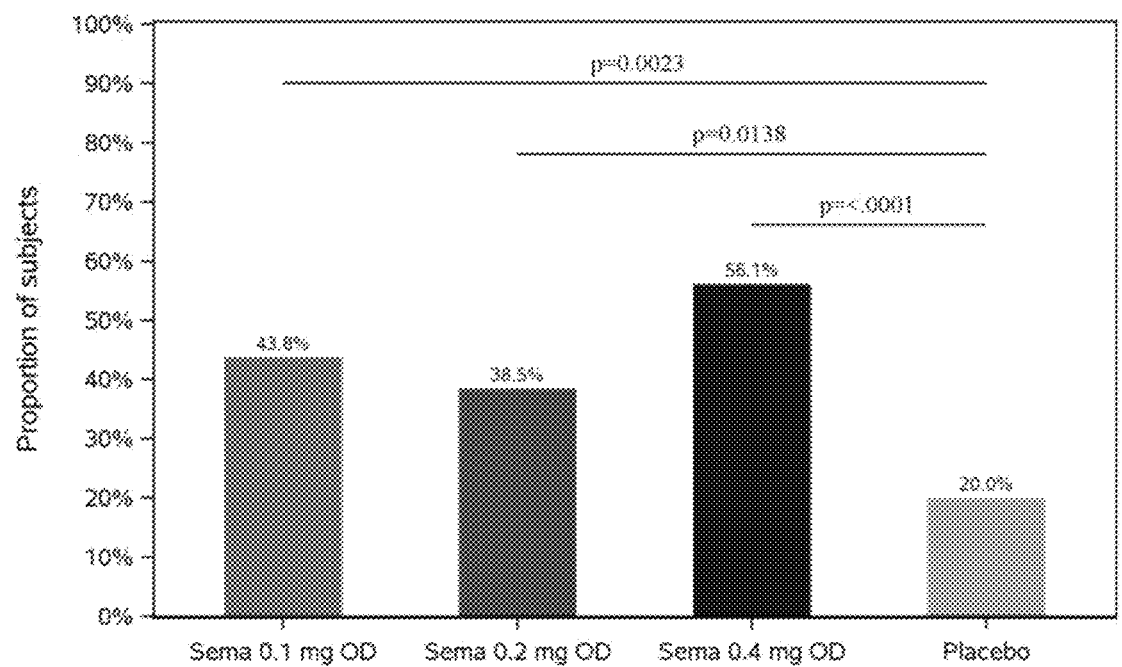
FIG. 2 shows the observations of resolution of NASH and no worsening in liver fibrosis at end of trial following administration of semaglutide (sema) or placebo in subjects with NASH and liver fibrosis stage 1-3 at baseline as described in Clinical Trial A herein.

The results in Table 4B show that treatment with semaglutide resulted in histological resolution of non-alcoholic steatohepatitis in patients with NASH and fibrosis stage 1-3 or NASH and fibrosis stage 2-3. Resolution of NASH and no worsening in liver fibrosis was achieved by significantly more subjects compared to placebo for all tested semaglutide dosages based on subjects with liver fibrosis stage 1-3 at baseline; these results are also shown in FIG. 2. Resolution of NASH means that the subject no longer fulfils the NASH diagnosis criteria. Resolution of NASH and no worsening in liver fibrosis was achieved by significantly more subjects compared to placebo for all tested semaglutide dosages based on subjects with fibrosis stage 2 or 3. Resolution of NASH and no worsening in liver fibrosis was achieved by significantly more subjects compared to placebo for all tested semaglutide dosages based on subjects with fibrosis stage 1, fibrosis stage 2, or fibrosis stage 3. The results in Table 4B also show significant improvement of resolution of NASH and no worsening in liver fibrosis compared to placebo for the 0.4 mg once daily semaglutide dosage.

TABLE 5

Worsening of liver fibrosis stage determined via liver biopsy at end of trial compared to baseline, based on all randomised subjects

| | Semaglutide OD | | | Placebo |
|---|---|---|---|---|
| | 0.1 mg | 0.2 mg | 0.4 mg | |
| Proportion of subjects (%) | 10.0 | 7.7 | 4.9 | 18.8 |

Data are based on all randomised subjects with all available assessments included regardless of treatment status. Subjects with missing data are handled as having no-change.

The results in Table 5 show that a lower proportion of subjects across all semaglutide dosages tested had worsening of liver fibrosis stage compared to placebo.

TABLE 6

Change in enhanced liver fibrosis (ELF) at end of trial compared to baseline relative to placebo, based on all randomised subjects and results provided as [ETD [95% CI range] p value]

| Semaglutide OD | | |
|---|---|---|
| 0.1 mg | 0.2 mg | 0.4 mg |
| −0.35 [−0.57; −0.14] p = 0.0012 | −0.40 [−0.62; −0.18] p = 0.0003 | −0.57 [−0.79; −0.36] p ≤ 0.0001 |

Data are based on all randomised subjects with all available assessments included regardless of treatment status. Estimated treatment differences (ETD) relative to placebo and two-sided p-values are from an ANCOVA with missing data multiple imputed from the placebo group.

The results in Table 6 show that semaglutide reduced ELF significantly more compared to placebo at all tested semaglutide dosages.

Overall, the results in Tables 1-6 show that semaglutide not only significantly decreased the severity of NASH compared to placebo but also resulted in a significantly larger group of patients no longer to fulfilling the criteria of the NASH diagnosis.

Results from Clinical Trial B

The results from Clinical Trial B as described above on liver steatosis determined by magnetic resonance imaging proton density fat fraction (MRI-PDFF) are shown in Tables 7-8 and are based on all randomised subjects.

TABLE 7

Change in liver steatosis by MRI-PDFF at trial week 24, 48 or 72 compared to baseline

| Week of trial | | Semaglutide 0.4 mg OD | Placebo |
|---|---|---|---|
| 24 | Estimated mean ratio * | 0.64 | 0.91 |
| | Semaglutide vs. placebo ** | 0.70 [0.59; 0.84] p = 0.0002 | |
| 48 | Estimated mean ratio * | 0.42 | 0.89 |
| | Semaglutide vs. placebo ** | 0.47 [0.36; 0.60] p ≤ 0.0001 | |
| 72 | Estimated mean ratio * | 0.42 | 0.83 |
| | Semaglutide vs. placebo ** | 0.50 [0.39; 0.66] p ≤ 0.0001 | |

* Estimated mean ratio to baseline based on an analysis of the relative endpoint calculated as value at landmark visit (i.e. at week 24, 48 or 72 of trial) divided by value at baseline.
** [ETR [95% CI range] p value].

ETR: Estimated treatment ratio. CI: Confidence interval. Data are based on all randomised subjects with all available assessments included, which per design are assessed while subjects are treated with randomised drug. Estimates and two-sided p-values are from a Mixed Model for Repeated Measurements.

The results in Table 7 show that semaglutide significantly reduced liver steatosis. Already at 24 weeks of trial semaglutide reduced liver steatosis by 30% compared to placebo and at 48 and 72 weeks of trial semaglutide reduced liver steatosis by about 50% compared to placebo.

TABLE 8

Proportion of subjects [% (p value vs. placebo)] with 30% or greater reduction in liver steatosis by MRI-PDFF at trial week 24, 48 or 72 compared to baseline

| Week of trial | Semaglutide 0.4 mg OD | Placebo |
|---|---|---|
| 24 | 64.7 (p = 0.0006) | 21.2 |
| 48 | 76.5 (p = 0.0001) | 30.3 |
| 72 | 73.5 (p = 0.0006) | 33.3 |

Data are based on all randomised subjects with all available assessments included, which per design are assessed while subjects are treated with randomised drug. Proportions and two-sided p-values are from a logistic regression model with missing data imputed by predicted values from a Mixed Model for Repeated Measurements with MRI-PDFF as continuous response.

The results in Table 8 show that at least 30% reduction in liver steatosis was achieved with semaglutide in about 65% of subjects at 24 weeks of trial and in about 74-77% of subjects at 48 and 72 weeks of trial, these results are statistically significant compared to placebo.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of treating non-alcoholic steatohepatitis (NASH), comprising administrating semaglutide subcutaneously in an amount of about 2.4 mg per week to a subject diagnosed with NASH, wherein the administering results in an improvement in lobular inflammation.

2. The method according to claim 1, wherein the subject does not have cirrhosis.

3. The method according to claim 1, wherein the method further comprises chronic management of NASH.

4. The method according to claim 1, wherein the semaglutide is the sole active ingredient administered to the subject.

5. The method according to claim 1, wherein the semaglutide is administered in an amount of 2.4 mg per week.

6. The method according to claim 5, wherein the semaglutide is administered once daily or less frequent.

7. The method according to claim 6, wherein the semaglutide is administered once weekly.

8. The method according to claim 1, wherein the method provides no worsening of liver fibrosis in the subject.

9. The method according to claim 1, wherein the semaglutide is administered in a pharmaceutical composition in the form of an aqueous solution comprising one or more pharmaceutically acceptable excipients.

10. The method according to claim 9, wherein the pharmaceutical composition is an aqueous solution comprising about 1.0 mg/ml semaglutide, about 1.42 mg/ml disodium hydrogen phosphate dihydrate, about 14.0 mg/ml propylene glycol, about 5.50 mg/ml phenol, and is at a pH of about 7.4.

11. A method of treating non-alcoholic steatohepatitis (NASH), comprising administrating of semaglutide subcutaneously to a subject diagnosed with NASH, wherein the subject has (i) portal/perisinusoidal fibrosis or (ii) perisinusoidal and portal/periportal fibrosis, wherein the semaglutide is administered in an amount of about 2.4 mg per week, and wherein the administering results in an improvement in lobular inflammation.

12. The method according to claim 11, wherein the semaglutide is administered in an amount of 2.4 mg per week.

13. The method according to claim 12, wherein the semaglutide is administered once weekly.

14. The method according to claim 13, wherein the semaglutide is the sole active ingredient administered to the subject.

15. The method according to claim 13, wherein the semaglutide is administered in a pharmaceutical composition in the form of an aqueous solution comprising one or more pharmaceutically acceptable excipients.

16. The method according to claim 15, wherein the pharmaceutical composition is an aqueous solution comprising about 1.0 mg/ml semaglutide, about 1.42 mg/ml disodium hydrogen phosphate dihydrate, about 14.0 mg/ml propylene glycol, about 5.50 mg/ml phenol, and is at a pH of about 7.4.

\* \* \* \* \*